United States Patent [19]

Hajost et al.

[11] 4,388,920
[45] Jun. 21, 1983

[54] VARIABLE POSITION KNEE IMMOBILIZER

[75] Inventors: Mark J. Hajost; Robert L. Crevling; Fred B. Powell, all of Greenwood, S.C.

[73] Assignee: Professional Medical Products, Inc., Greenwood, S.C.

[21] Appl. No.: 314,900

[22] Filed: Oct. 26, 1981

[51] Int. Cl.³ .............................................. A61F 3/00
[52] U.S. Cl. ..................................... 128/80 C; 128/88
[58] Field of Search ................ 128/80 C, 80 F, 87 R, 128/88, 165

[56] References Cited

U.S. PATENT DOCUMENTS 2,545,843  3/1951  Cohan ............................... 128/80 F
4,013,070  3/1977  Harroff ............................ 128/80 C

FOREIGN PATENT DOCUMENTS 13630 of 1901 United Kingdom ............. 128/80 C

Primary Examiner—John D. Yasko
Attorney, Agent, or Firm—Luke J. Wilburn, Jr.; Wellington M. Manning, Jr.

[57] ABSTRACT

A wraparound immobilizer including a stiffener support which is rotatable and lockable to accommodate the varying positions of a patient's knee.

5 Claims, 3 Drawing Figures 4,388,920

VARIABLE POSITION KNEE IMMOBILIZER

SUMMARY OF THE INVENTION

This invention relates to an orthopedic device for immobilizing the knee in varying positions.

The immobilizer includes a flexible cover which wraps around the patient's knee. A support stiffener is attached to and extends beneath the rear of the cover in a position in alignment with the leg and behind the knee. The support stiffener has a top section above the knee, and a bottom section below the knee. These sections are pivotally connected at the middle of the knee so as to be capable of varying the angle between the sections in order to position the knee in varying positions. Means are provided to lock the support stiffener in varying positions so as to immobilize the patient's knee.

Accordingly, it is the object of this invention to provide an immobilizer for the knee in varying positions.

Another object of this invention is to provide a wraparound immobilizer for the knee, which can be locked and unlocked in varying positions.

Still another object of this invention is to provide a wraparound immobilizer for varying positions of the knee, which can be simply applied to the patient.

Other objects of the present invention will become apparent as the description proceeds.

BRIEF DESCRIPTION OF THE DRAWINGS

A preferred embodiment of this invention has been chosen for illustration and description wherein.

DESCRIPTION OF A PREFERRED EMBODIMENT

Figure 1:
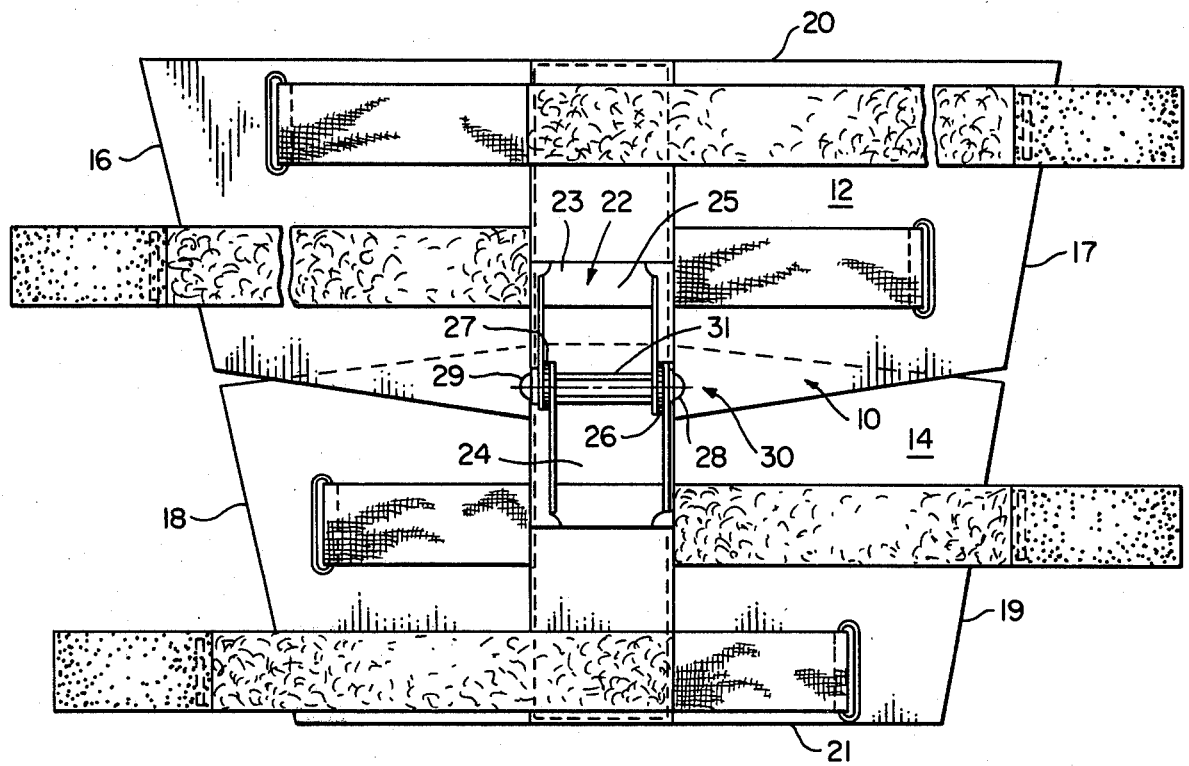
FIG. 1 is a bottom view of the outside of the knee immobilizer shown in detached form.
Figure 2:
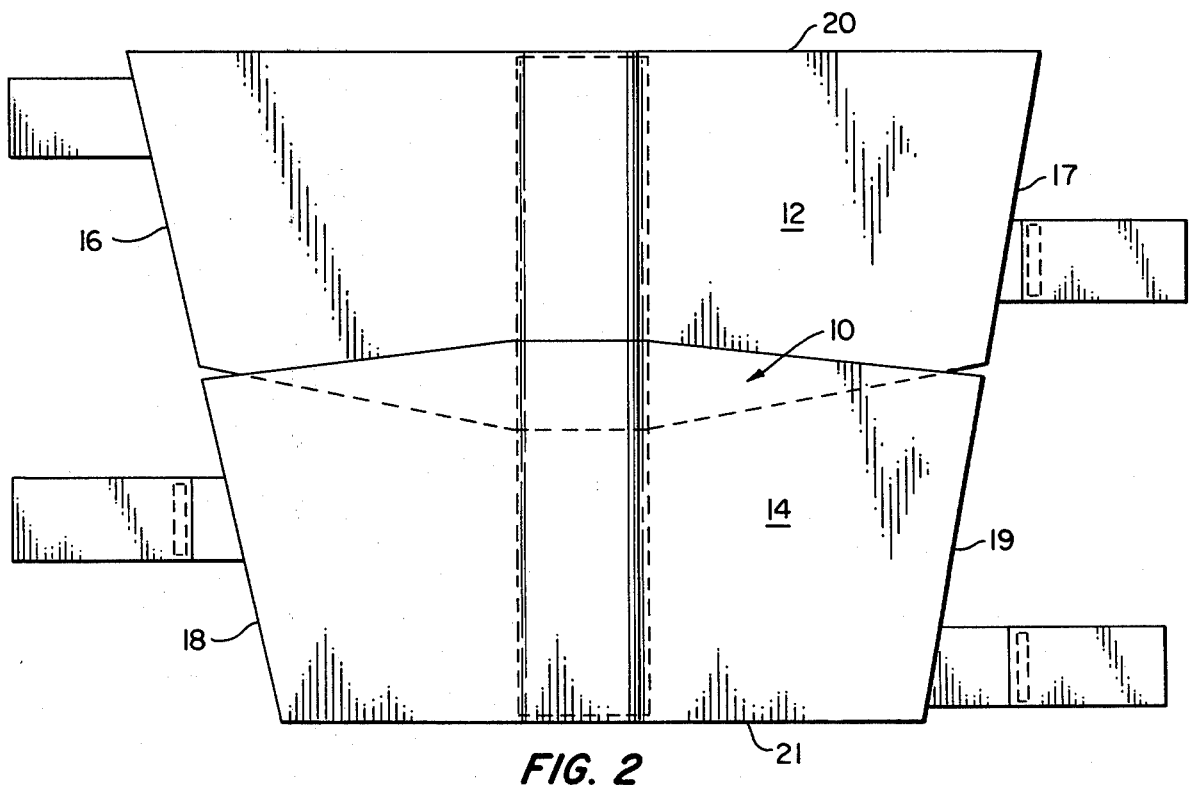
FIG. 2 is a top view of the inside of the knee immobilizer shown in detached form.
Figure 3:
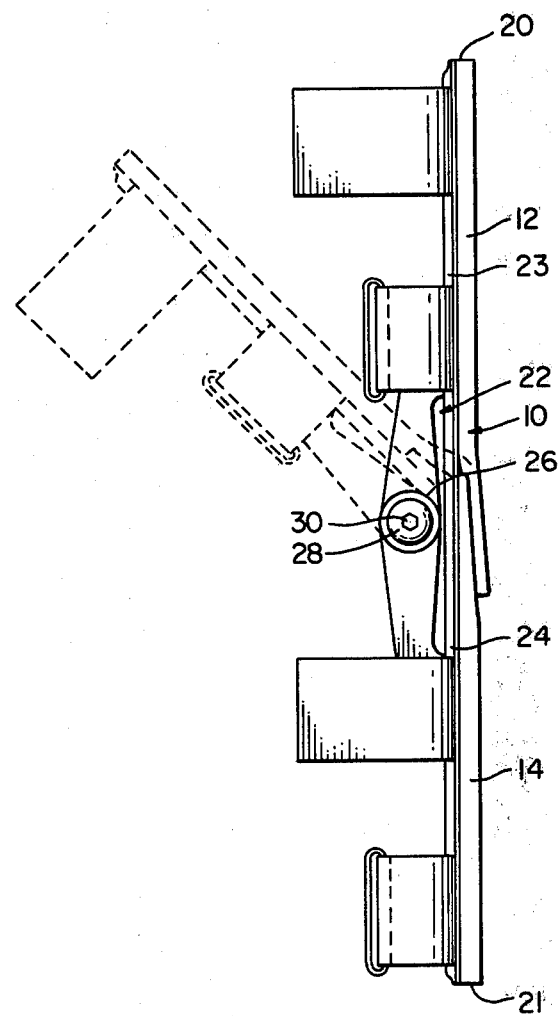
FIG. 3 is a side view of the support stiffener shown in varying positions to immobilize the knee of the patient.

The preferred embodiment illustrated is not intended to be exhaustive or to limit the invention to the precise form disclosed. It is chosen to be described in order to best explain the principles of the invention and its application so as to enable others skilled in the art to best utilize the invention.

The immobilizer includes a flexible cover 10. Cover 10 includes an upper section 12 extending from the thigh down over the knee of the patent, and a lower section 14 extending from the knee down over the calf of the patient. Upper section 12 slightly overlaps lower section 14 at the rear of the knee of the patient. To accommodate the anatomical shape of the patient's knee, side edges 16 and 17 of the upper section 12, and the side edges 18 and 19 of the lower section 14, taper downward from the top edge 20 of upper section 12 to the bottom edge 21 of lower section 14, with the cover assuming a trapezoidal appearance when detached in planar form. Cover 10 may be formed of a variety of materials, such as a polyvinyl foam construction having a looped pile material applied to its outer surface. A stiffener support 22 in alignment with the leg and behind the knee of the patient is attached to the outside of the cover 10, positioned midway between the side edges 16 and 17 of the upper section 12, and the side edges 18 and 19 of the lower section 14; and extending from adjacent to the top edge to down to adjacent to the bottom edge 21. The stiffener support 22 is secured in position by being sewn, or inserted within pockets, or otherwise appropriately affixed to the cover 10. The stiffener support consists of an upper part 23 and a lower part 24, that are interchangeable. That is, the parts themselves are neuter in that either may be the upper part or the lower part. Each part 23 and 24, of the stiffener support 22 consists of a metallic plate 25 with two disks 26 and 27 perpendicular to the plate 25 and on an extension 30 centered approximately ⅝ inch to the rear of the cover 10. The disks 26 and 27 are serrated or toothed with 45 individual slots radial on 360 degrees. One disk 26 is flush with the edge of the metallic plate 25 with the serrations facing toward the second disk 27. The second disk 27 is inset from the other edge of the metallic plate 25 by the thickness of one serrated disk or approximately 0.156±0.004 inch with its serrated side facing in the same direction as the first disk 26. In this manner another part of the same design can be mated with the serrated disks axially engaged together with pivot pins, in this case two ¼ inch-20 bolts, 28, 29 thereby preventing any rotation when the bolts are tightened against the spacer 31. When the bolts are loosened the upper part 23 and the lower part 24 can be rotated from 180 degrees down to 0 degrees in order to adjust the knee immobilizer to accommodate the varying positions of the patient's leg.

It is preferred that the securement means for the support stiffener 22 also carry securing means for fastening the cover 10 about the patient's knee. Securing means such as straps or buckles can be sewn directly to cover 10.

It is to be understood that the invention is not to be limited to the details above given, but may be modified within the scope of the pending claims.

What is claimed is:

1. A variable position knee immobilizer comprising:
    a flexible cover having upper and lower sections each in planar orientation having upper and lower edges and opposite side edges and adapted to be wrapped about and surround the thigh and calf portions of a patient's leg;
    securing means connected to said upper and lower sections of said cover for fastening the cover around the patient's leg above and below the knee; and
    stiffener support means comprising upper and lower elongate, interconnected generally flat plates operatively connected to corresponding upper and lower sections of the cover generally centrally of their side edges and extending from adjacent the top edge to the bottom edge of each section to be located along the back of the leg generally parallel to the length of the leg with adjacent ends of the plates being positioned directly behind the knee, and means pivotally interconnecting the adjacent ends of the plates for rotatably positioning the plates and the upper and lower sections of the cover, said pivotal interconnecting means including means for locking the plates at varying positions of the patient's knee to immobilize the leg in such positions.

2. The knee immobilizer of claim 1 wherein said pivotal interconnecting means comprise spaced disk portions on the adjacent ends of each plate extending perpendicular to the plane of the plate, the disk portions on one of said plates engaging corresponding disk portions on the other of said plates, and said locking means including pivot pin means connecting disk portions of one plate to respective disk portions of the other plate and being adjustable to grippingly secure the same together and prevent relative movement of the plates.

3. The knee immobilizer of claim 2 wherein said locking means further includes serrations on opposed contiguous surfaces of said disk portions for frictional engagement to secure said plates against relative movement upon gripping engagement by said pivot pin means.

4. The knee immobilizer of claim 3 wherein said pivot pin means includes a pair of bolts extending through openings in respective engaged disk portions of the plates and engaging spacer means extending between the spaced disk portions of the plates, said bolts being individually adjustable to grip said disk portions and thereby maintain said plates in fixed position relative to each other.

5. The knee immobilizer of claim 1 wherein said upper and lower plates and disk portions thereof are of substantially identical construction to facilitate their manufacture and interchangeable use in the knee immobilizer.

* * * * *